United States Patent
Magill

[11] Patent Number: 5,749,365
[45] Date of Patent: May 12, 1998

[54] HEALTH MONITORING

[76] Inventor: Alan Magill, 1 Russel Chambers, Covent Gardens, London, United Kingdom, WC2E 8AA

[21] Appl. No.: 232,147
[22] PCT Filed: Nov. 9, 1992
[86] PCT No.: PCT/GB92/02064
§ 371 Date: May 5, 1994
§ 102(e) Date: May 5, 1994
[87] PCT Pub. No.: WO93/08734
PCT Pub. Date: May 13, 1993

[30] Foreign Application Priority Data

Nov. 7, 1991 [GB] United Kingdom ............... 9123638

[51] Int. Cl.$^6$ ........................................ A61B 05/04
[52] U.S. Cl. ........................ 128/671; 128/721; 128/725; 128/903
[58] Field of Search .................... 128/721, 722, 128/725, 696, 670, 668, 671, 903

[56] References Cited

U.S. PATENT DOCUMENTS

| | | | |
|---|---|---|---|
| 4,245,651 | 1/1981 | Frost | 128/721 |
| 4,471,354 | 9/1984 | Smith | 128/631 |
| 4,572,197 | 2/1986 | Moore et al. | 128/721 |
| 4,827,943 | 5/1989 | Bornn et al. | 128/668 |
| 4,909,260 | 3/1990 | Salem et al. | 128/671 |
| 4,960,118 | 10/1990 | Pennock | 128/721 |
| 5,058,597 | 10/1991 | Onoda et al. | 128/704 |
| 5,064,192 | 11/1991 | Smith | 128/721 |
| 5,125,412 | 6/1992 | Thorton | 128/671 |
| 5,131,399 | 7/1992 | Sciarra | 128/721 |
| 5,235,989 | 8/1993 | Zomer | 128/721 |
| 5,241,300 | 8/1993 | Buschmann | 340/573 |
| 5,335,664 | 8/1994 | Nagashima | 128/696 |
| 5,423,328 | 6/1995 | Gavish | 128/721 |

FOREIGN PATENT DOCUMENTS

| | | |
|---|---|---|
| 1908652 | 2/1963 | Germany . |
| 3444635 | 12/1984 | Germany . |
| 1 596 298 | 8/1981 | United Kingdom . |
| 2081454 | 2/1982 | United Kingdom . |
| 8802237 | 7/1988 | WIPO . |
| 8902246 | 3/1989 | WIPO ............... 128/670 |

*Primary Examiner*—Robert Nasser
*Attorney, Agent, or Firm*—Keck, Mahin & Cate

[57] ABSTRACT

A method for monitoring vital signs of a human or animal subject includes clothing the subject in an elastically deformable shirt or undershirt, removably attaching a carrier carrying a sensor to the shirt or undershirt, adjacent the thoracic and abdominal regions of the subject, sensing elastic deformations of the shirt or undershirt corresponding to one or more of the group of vital signs including respiration, heart function, heart rhythm, generating electrical signals representative of the deformations, and transmitting the signals to a remote receiver for processing.

25 Claims, 4 Drawing Sheets

HEALTH MONITORING

The present invention relates to health monitoring, and is especially concerned with monitoring one or more vital signs of a human or animal subject.

Facilities for monitoring vital signs (embracing respiration, pulse, body temperature and blood pressure) of a subject are readily available in the context of a hospital or clinic. Whereas such facilities can, as a general matter, also be used and adapted for monitoring a subject out of that context, for example in the home environment, the equipment involved is normally not only expensive, but also obtrusive, cumbersome and inconvenient to an extent that its use is unacceptable or creates an undesirable intrusion into everyday life.

It is one of the objects of the present invention to facilitate the monitoring of vital signs in a less obtrusive, cumbersome and inconvenient manner than with known equipment.

According to one aspect of the present invention there is provided a method for monitoring vital signs of a human or animal subject, wherein the subject wears a vest in the form of a garment that has stretch both laterally and longitudinally of the subject's body to fit the body closely, elastic deflections of the vest related to respiratory and/or heart functions of the subject are sensed in both the thoracic and abdominal regions of the subject by sensors that are carried by a common carrier attached to the vest, and signals dependent on the sensed deflections are transmitted for reception and analysis remotely of the subject. The term vest is used in a generic sense and means shirt or undershirt.

According to another aspect of the invention a system for monitoring vital signs of a human or animal subject, comprises a vest for wear by the subject in the form of a garment that has stretch both laterally and longitudinally of the subject's body to fit the body closely, sensors that are carried by a common carrier attached to the vest for sensing in both the thoracic and abdominal regions of the subject elastic deflections of the vest related to the subject's respiratory and/or heart functions, and means for transmitting signals dependent on the sensed deflections for reception and analysis remotely of the subject.

The method and system of the invention are of especial advantage where monitoring is to be carried out in circumstances, which may occur in the environment of a hospital or clinic, but may be more significant in the home environment, where the presence and use of conventional health monitoring equipment is likely to cause distraction and anxiety for the subject concerned, and, possibly also, for those involved with the subject. For example, with apnoea-monitoring of a baby in its home environment, there is a risk that the visible presence of monitoring equipment will have an adverse effect on the welfare of both the infant and its parents.

With the method and system of the present invention there is the advantage that monitoring can be carried out in an unobtrusive manner, and the vest worn can be of a conventional, everyday form that can be laundered in the usual way. More particularly, the use of a common carrier attached to the vest and carrying the sensors for sensing the elastic deflections, facilitates concealment of the sensors. In this respect moreover, the carrier may have an external decorative form which not only hides the sensors but diverts attention from its principal purpose. There is, accordingly, the advantage that monitoring can be carried out against the background of normal, everyday life without the intrusion of unusual and cumbersome objects that might give cause for apprehension or concern to the subject and/or for the subject's welfare.

There is particular advantage where all cable or other connections to the baby or other subject are eliminated by using electromagnetic-wave transmission of signals from the vest to the remote, monitoring location. The means for such transmission may also be carried by, and concealed with the sensors within, the common carrier.

The common carrier, which may be attached to the inside or outside of the vest, is preferably provided in the form of a patch that is releasably attached to the vest; this facilitates change of vest and laundering, and replacement of the patch in the event of malfunction. Releasable attachment may be achieved by use of fabric fastening (for example, fastening of the kind sold under the Registered Trade Mark VELCRO) based on the inter-engagement of hook fibres with other fibres, or by use of press-stud, laced or button attachment.

Where press-stud, laced or button attachment is used, the appropriate location for securing the patch to the vest will require no further definition, but where other attachment is used, the relevant location can be defined by marking included with the vest. However, by suitably dimensioning, configuring or otherwise defining the patch, it may be possible to avoid the necessity for any definition of location on the vest itself, and in any event, for most situations the precise location of the sensors on the body will not be critical. The fact that the sensors are carried as one by the carrier, maintains their relative positions and enables their appropriate placement relative to the subject's body to be executed in a simple and convenient, single operation.

As an alternative, the patch may be accommodated under a flap or within a pocket of the vest, so that its location on the vest is clearly established. But the use of a flap or pocket also has the benefit of at least partially concealing the patch and limiting the possibility of it being inadvertently detached by the subject.

Where fabric fastening based on fibre hook-and-eye interengagement is used for attaching the patch to the vest, and, possibly, also for holding a covering flap or pocket closed upon it, the structure of the vest may be such that it naturally provides the necessary 'eye' fibres for engagement by the hooks in the fastening, or can be fluffed up to do so where appropriate. The vest in this regard may be of cotton and preferably of a seamless, knitted form so as to have good contour-conforming, stretch qualities.

The elastic deflections of the vest may be sensed by strain gauges that involve piezo-electric film and are arranged to respond, for example, to the extension and contraction of the vest in the thoracic and abdominal regions respectively, in accordance with the subject's breathing pattern and heart hydraulics. The signals provided by these, or by other sensors responsive to the elastic deflections, may be processed, for example using adaptive filtering techniques, to provide representations of thoracic-abdominal motion suitable for the detection of loss of abdominal-thoracic synchrony. At least part of the processing may be carried out by an electrical circuit carried by the common carrier attached to the vest.

The common carrier, whether in the form of a patch releasably attached to the vest or otherwise, may be of a laminated construction that includes a printed-circuit substrate on which the sensors are mounted. Means, for example in the form of a thermistor, may be included for sensing the subject's body temperature. When the carrier is attached to the outside of the vest, a small hole may be provided in the vest to enable the thermistor or other temperature-sensing means to project through to make contact with the subject's skin, or to have unobstructed exposure to the skin, but it is generally adequate for sensing to be made via the vest without special adaptation.

Methods and systems for monitoring vital signs of a human subject in accordance with the present invention, will now be described, by way of example, with reference to the accompanying drawings in which.

The methods and systems to be described with reference to the drawings are concerned with monitoring physiological conditions, such as heart activity, respiration and body temperature, of a baby in the context of a home environment, during sleep. However, the methods and systems of the invention may be used in a more general context than this; for example, the principles involved may be used for physiological monitoring of adults, whether at home or in hospital, during athletic or hazardous pursuits, and may also be used for monitoring animal subjects.

Figure 1:
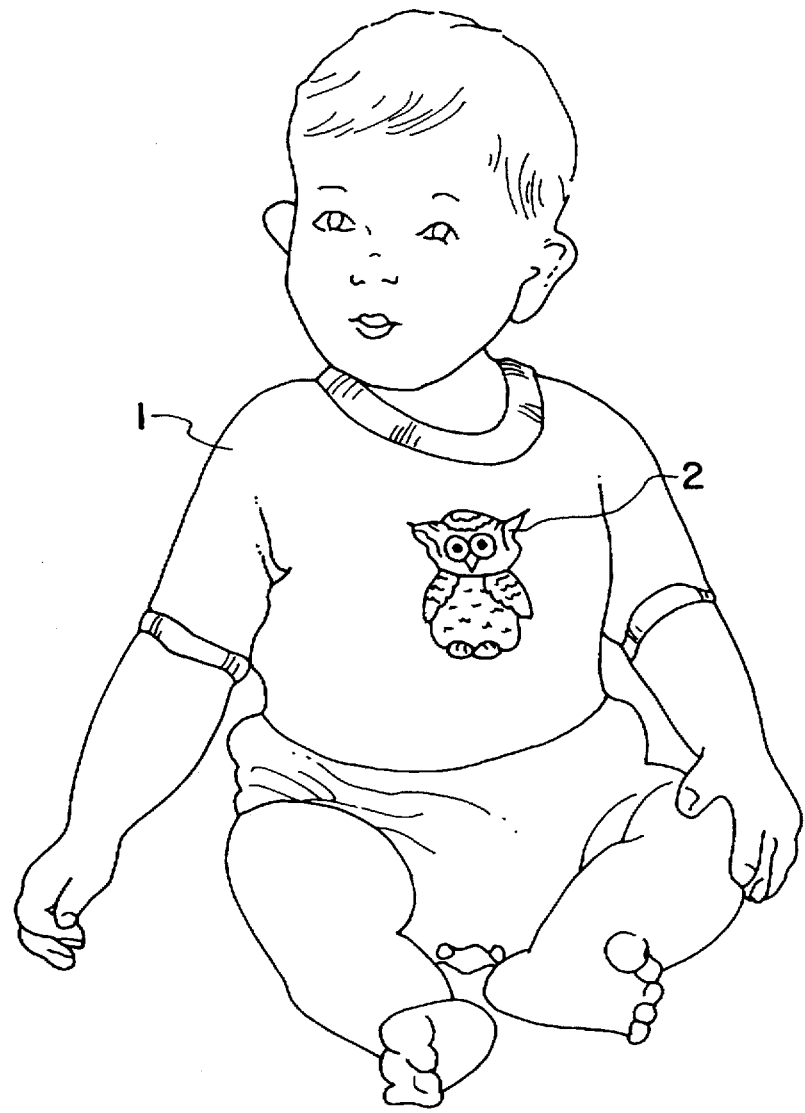
FIG. 1 is view of a baby wearing a vest forming part of a first health-monitoring system in accordance with the present invention.

Referring to FIG. 1, the baby wears a closely-fitting cotton vest 1 of conventional style. The vest 1, which is seamless and machine-knitted to the general shape of the baby's torso, has stretch both longitudinally and laterally of the baby's body so that it hugs the upper part of the body closely from shoulders to hips. The bi-directional stretch and seamlessness are of especial advantage in retaining the vest closely against the body in the abdominal region without significant tenting, that is to say, lifting up of the vest 1, over the baby's nappies or diapers.

A fabric patch 2 of decorative shaping and colouring (shown in FIG. 1 with the design format of an owl) is attached to the front of the vest 1. The patch 2, which is some 50 mm in width and some 100 mm in length, is of laminate construction and is attached to the vest 1 to bridge the baby's thoracic and abdominal regions. An electrical circuit is incorporated within the laminate of the patch 2 for sensing manifestations of the baby's vital signs in these regions and transmitting electromagnetic-wave signals in accordance therewith for reception and monitoring remotely of the baby.

Figure 3:
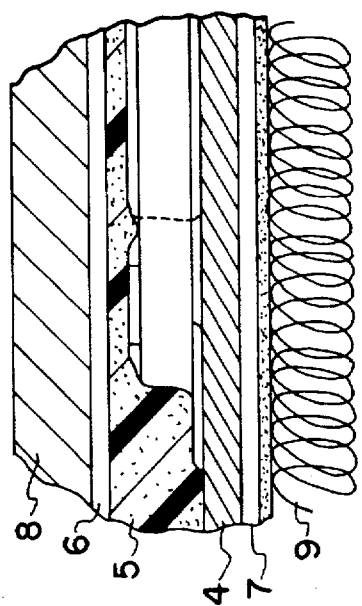
FIGS. 2 and 3 illustrate the laminate construction of a carrier patch that is worn on the vest of FIG. 1 and incorporates an electrical circuit for use in monitoring the health of the baby, FIG. 2 being an exploded view showing the laminate split apart layer from layer, and FIG. 3 showing a cross-section of part of the patch to an enlarged scale.
Figure 2:
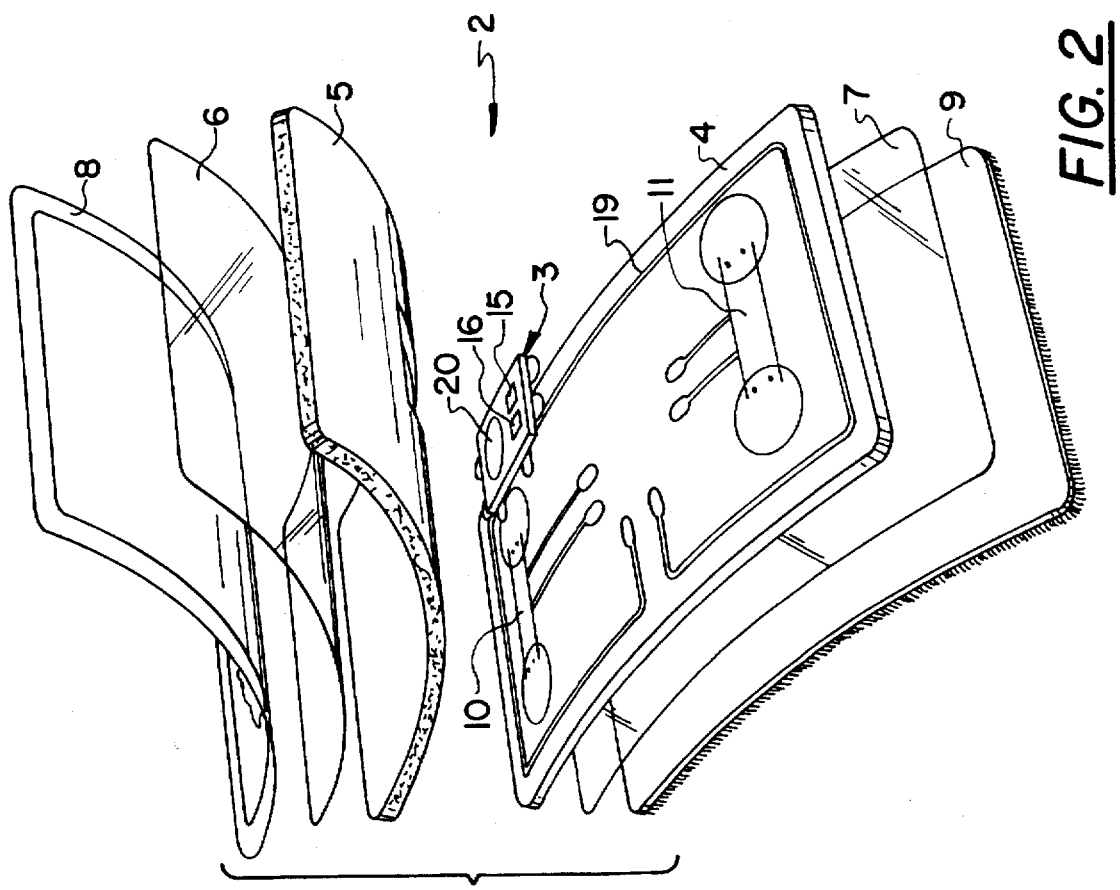

The construction of the patch 2 is illustrated in FIGS. 2 and 3, and will now be described. The patch 2 is shown in FIG. 2 for ease of representation, as though having a rectangular configuration rather than the owl-shaping of FIG. 1.

Referring to FIGS. 2 and 3, the electrical circuitry of the patch 2 includes a printed-circuit board 3 carried by a flexible substrate 4. The substrate 4 and the board 3 are cushioned from impact-damage by a covering layer 5 of foamed-plastics material, and the substrate 4 with its covering layer 5 are sandwiched between two flexible waterproof-sheets 6 and 7 that are bonded to the layer 5 and substrate 4 respectively. The sheets 6 and 7 are bonded together around their peripheries so as to encapsulate the substrate 4 and the board 3. A top, outer layer 8 of the patch 2 is bonded to the sheet 6, and the sheet 7 is bonded to a backing sheet 9 by which the patch 2 is attached to the vest 1.

The layer 8 is of a fabric that carries the decorative design (an owl in FIG. 1), and whereas the backing sheet 9 may be fastened to the vest 1 by means of press-stud, laced or button fixing, it is preferably, as illustrated, secured by fabric fastening based on fibre hook-and-eye inter-engagement (such as sold under the Registered Trade mark VELCRO). More particularly, the sheet 9 is of a stretchable fabric having its exposed, back surface formed with upstanding fibres of hook configuration that engage with the fibres of the vest-material to secure the sheet 9, and with it the circuitry of the substrate 4, to the vest 1 firmly but releasably.

The appropriate location on the vest 1 for attachment of the patch 2 may, if desired, be delineated by lines or other markings printed or otherwise incorporated in the vest 1. Because of the fabric fastening, the patch 2 is very easily attached merely by laying it in place and applying gentle pressure to consolidate the hook-fibre engagement of the backing 9 with the vest 1; removal is carried out simply by gripping the patch 2 by hand and stripping it away. The attachment of the patch 2 anchors the substrate 4 to the vest 1 so that it is subject to strain in accordance with the elastic extensions and contractions of the vest-material as the baby breathes in and out. These deflections of the vest are sensed by two parallel strips 10 and 11 of piezo-electric film that are bonded in face-to-face contact with the substrate 4 to sense bending and/or stretching. The strips 10 and 11 are spaced from one another longitudinally of the patch 2 (normally, by more than 50 mm) to function as strain gauges for the thoracic and abdominal regions of the baby's body, within the electrical circuitry carried within the patch 2.

Figure 4:
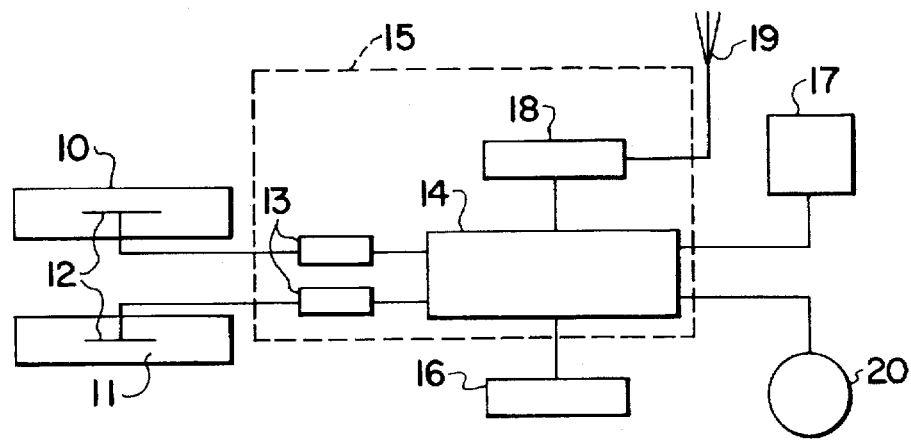
FIG. 4 is a block schematic diagram of the electrical circuit incorporated in the patch of FIGS. 2 and 3.

The electrical circuitry of the patch 2 is shown schematically in FIG. 4, and, as shown in FIG. 4, the signals supplied from electrodes 12 of the film strips 10 and 11 are passed via respective pre-amplifiers 13 to a microprocessor 14. The pre-amplifiers 13 and the microprocessor 14 form part of a signal-processing chip 15 that, together with a controller 16, is mounted on the printed-circuit board 3 of the substrate 4. The microprocessor 14 is controlled by the controller 16 to derive health-related data in accordance with the output signals of the pre-amplifiers 13 and a signal dependent on the baby's body-temperature supplied from a thermistor 17 (not shown in FIG. 2).

The health-related data derived by the microprocessor 14 is supplied to a signal-transmitter 18 of the chip 15, for low-power electromagnetic-wave transmission from an inductive-loop antenna 19 to a remote receiver. The loop antenna 19 is printed on the substrate 4 to encircle the board 3 and the strips 10 and 11. The board 3 carries a re-chargeable battery 20 for powering the patch 2, and the whole of the circuitry within the loop-antenna 19 is protected from external electrical interference by screening on the sheets 6 and 7.

The location of the patch 2 on the vest 1 is such as to place the film-strips 10 and 11 extending laterally of the baby's thorax and abdomen respectively, so that the signals generated by the strips 10 and 11 are dependent on the respiratory movements in those respective regions; the strips 10 and 11 also respond to the baby's heart beat as conveyed via the rib cage and abdomen respectively. Moreover, the signals generated by the strips 10 and 11 include components that are dependent generally on the hydraulics of the baby's heart, and respiratory sounds, in particular, wheezing. These signals are filtered within the pre-amplifiers 13 to remove unwanted noise before being passed to the microprocessor 14 along with the temperature signal from the thermistor 17.

The thermistor 17, which is of miniature bead form, is preferably located on the substrate 4 in the region of the abdomen, over the baby's liver. It has been found that it is not necessary for the thermistor 17 to be in direct contact with the baby's skin for substantially accurate monitoring of body temperature, and changes in temperature, to be facilitated.

The signals supplied from the pre-amplifiers 13 and the thermistor 17 are processed within the microprocessor 14 to derive digital data in accordance, principally, with thoracic-related activity, abdomen-related activity and body temperature. The data is derived according to a program involving sampling and frequency analysis of the input signals and using data-compression techniques, and is supplied for transmission by the transmitter 18. The transmitter 18 is operable to transmit the data via the antenna 19 in periodic bursts, but this operation can be overridden to provide for continuous transmission when required.

The transmission from the antenna 19 is received at a station remote from the baby, for example, in a unit attached to the outside of the baby's cot or located elsewhere in the same or another room. A unit suitable for use at the remote station is illustrated schematically in FIG. 5 and will now be described.

Figure 5:
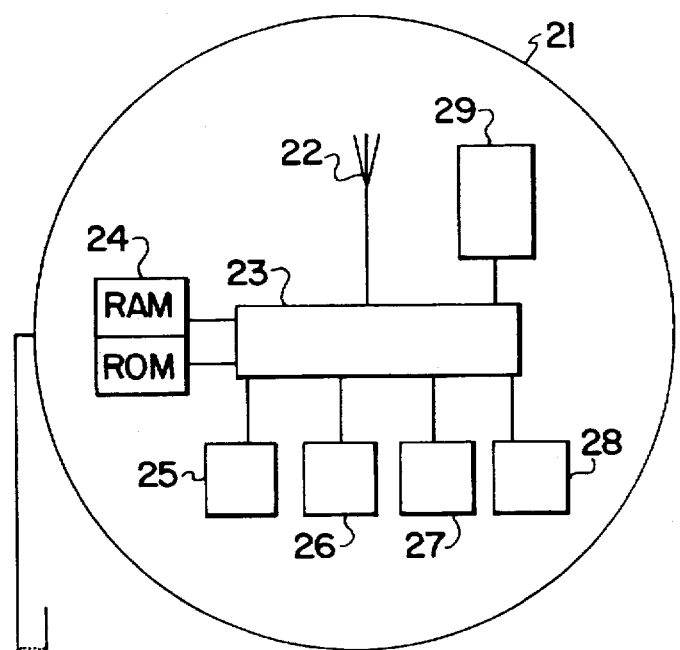
FIG. 5 is a block schematic diagram of the electrical circuit of a remote unit used in conjunction with the vest and its patch in monitoring the health of the baby of FIG. 1.
Figure 5:
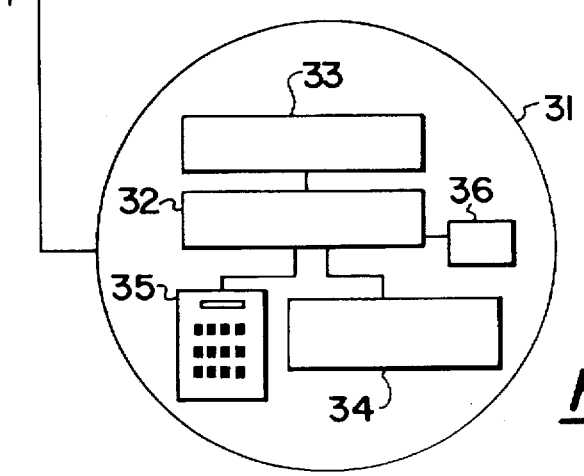

Referring to FIG. 5, a receiver unit 21 for location remotely of the baby includes an antenna 22 for receiving the data transmissions from the patch 2. The received data is supplied from the antenna 22 to a microprocessor 23 and is there submitted to adaptive filtering and other techniques for deriving signal representations dependent upon the baby's vital signs. These representations are written to a RAM section of memory 24 of the unit 21 for storage, and are continuously monitored within the microprocessor 23 for response to incipient conditions affecting the baby's welfare. More particularly in the latter respect, the representations are monitored by the microprocessor 23 against clinical criteria stored in a ROM section of the memory 24, and the unit 21 includes an alarm 25 that is triggered from the microprocessor 23 to provide both an audible and a visual warning signal whenever this is warranted. A digital display device 26 is also included for displaying values in accordance with whichever of the derived representations is selected using a selector device 27 of the unit 21.

The unit 21, which is powered by a re-chargeable battery 28, may (as shown in FIG. 5) also include, selectively, a VHF transmitter capsule 29. The transmitter capsule 29 is adapted to be inserted into the unit 21 and when so inserted converts the unit 21 to transmit information about the baby's physiological condition by VHF radio signals to a radio-receiver located at a distance and, for example, carried by a parent or nurse. Use of the capsule 29 in the unit 21 enables long-range communication to be achieved without locating a high-power transmitter on the baby.

One of the representations derived within the unit 21 and written to the RAM section of the memory 24, is that of the degree of the synchrony/asynchrony between the thoracic and abdominal respiratory motions of the baby. The microprocessor 23 acts in this to determine the relative phasing of the signals in accordance with the frequency and depth of breathing monitored by the piezo-electric strips 10 and 11. However, representations of the rate and tidal volume of respiration are also derived from these signals, and any components of them that are indicative of deterioration in respiration caused by wheezing or restriction of the baby's airway, are recorded. Furthermore, representations of pulse frequency and rhythm are derived together with representations of temperature and change of temperature, in accordance with the signals received from the patch 2.

A portable data logger 31 is connectable to the unit 21 to access the data stored in the RAM section of the memory 24. The data logger 31 includes, in addition to a processor 32, a digital-audio tape store 33 for receiving and retaining data from the memory 24 and storing it over a long period for detailed analysis. It may also include, as shown, a plotter 34 for providing a graphical display of the information accumulated, a key-pad 35 for entering data and making selections, and a modem 36 for down-loading data for computer analysis.

Data is normally transmitted from the transmitter 18 of the patch 2 in periodic bursts in order to conserve battery power. However, as indicated above, it is possible to override this operation of the transmitter 18 to provide continuous transmission. This is achieved by means of a magnetically-operated switch (not shown) incorporated in the circuitry of the patch 2 and connected to the transmitter 18. The setting of the switch determines whether the transmission is periodic or continuous and is changed simply by passing a magnet in one or the other direction over the patch 2. The switch may also be connected to the pre-amplifiers 13 so that when set for continuous transmission, the signal-filtering function carried out within the pre-amplifiers 13 is by-passed.

The sensing within the patch 2 of thoracic and abdominal movements, may be carried out using techniques other than the piezo-electric sensing involved in the film strips 10 and 11; for example, sensing based on the Hall effect, may be used. However, the use of piezo-electric film may be extended in that a single sheet of the film may replace the discrete strips 10 and 11, this film when printed with appropriately-conductive ink, not only providing the strain-gauge sensors required in the thoracic and abdominal regions (and possibly elsewhere too) but acting as the substrate for all the circuitry of the patch 2 in place of the substrate 4. The film in this latter case, as well as in the discrete-strip form, may be configured to respond to bending, perhaps to a greater extent than stretch; the response can be modified in this respect where the film is in the form of a double-film laminate, by varying the relative orientations with which the laminations are bonded together face to face.

The patch 2 is removable from the vest 1 to enable the vest 1 to be laundered without the possibility of damage to the electrical circuitry, and to enable easy replacement when the charge of the battery 20 is exhausted and in the event of circuit fault. However, the patch 2 may be attached to the vest 1 permanently if desired, and in either case, may be attached inside the vest 1 rather than on the outside. As an alternative, it may be accommodated under a flap or within a pocket of the vest, so as not only to locate it precisely, but at least partially to conceal it and to limit the possibility of it being detached by the baby. A health-monitoring system involving a vest with a flap or pocket to accommodate a patch in this way, is illustrated in FIG. 6, and will now be described.

Figure 6:
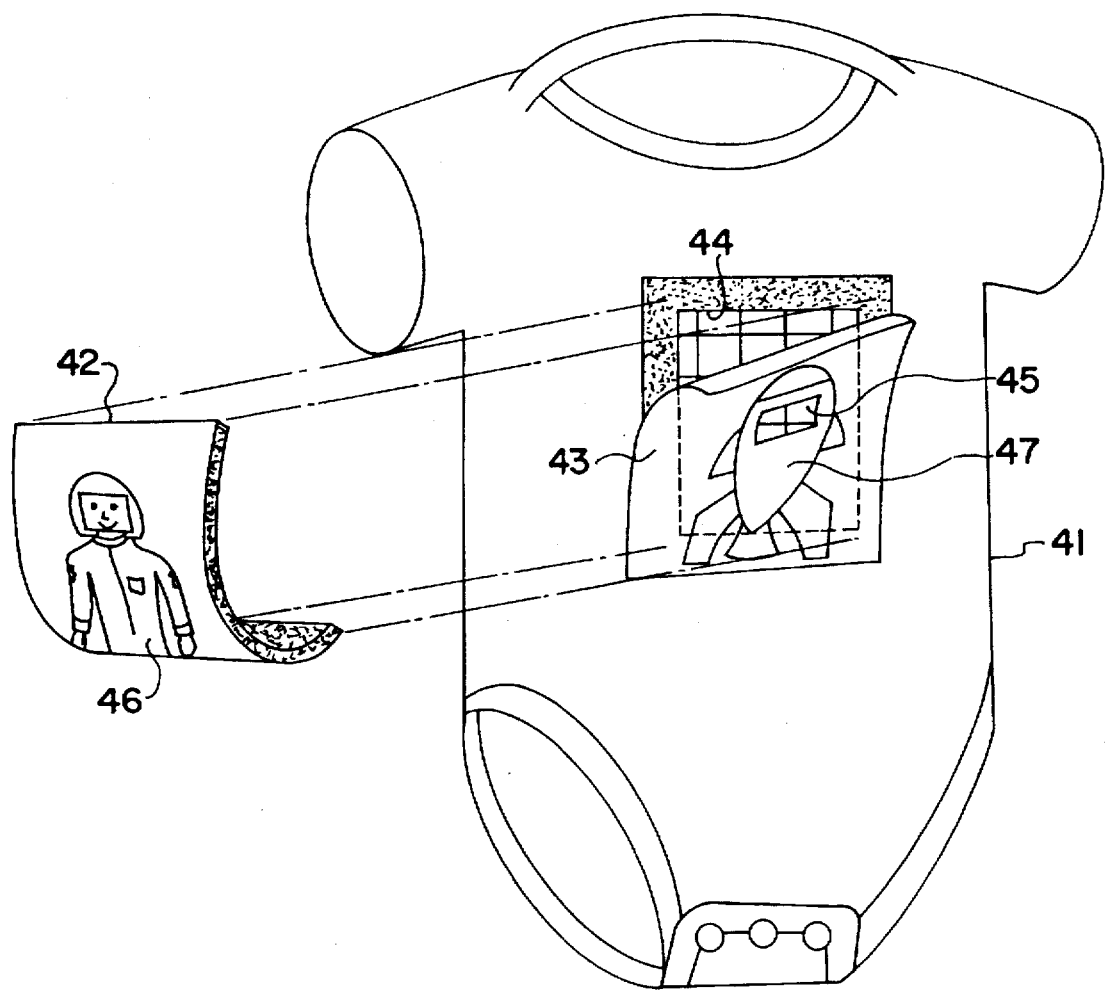
FIG. 6 shows a second system for the health-monitoring of a baby, in accordance with the present invention, with a carrier patch of the system removed from a flap-pocket of the vest.

Referring to FIG. 6, the vest 41 in this case has the same general stretch qualities as the vest 1 of FIG. 1, but the patch 42 used is inserted under a flap 43 that covers a partial opening 44 in the front. The opening 44 contributes to the stretch available in the vest 41 where sensing is to occur, and the patch 42 (which is essentially the same as the patch 2 described above) is inserted under the flap 43 bridging the opening 44. The patch 42 is attached by fabric hook-and-eye fastening to the margin of the vest 41 around the opening 44, and the flap 43 is closed over it; the flap 43 is held there, also by fabric hook-and-eye fastening to the vest 41 and, possibly, to the patch 42 too.

A small window 45 (in the form an aperture or a thinned portion) in the flap 43 is provided to reveal artwork 46 of the patch 42 and confirm its location on the vest 41. In the illustrated embodiment, the artwork 46 depicts a spaceman and the window 45 is located on the flap 43 within artwork 47 that depicts a spaceship, so that the head of the spaceman appears at the spaceship window 45 when the patch 42 is correctly in place.

I claim:

1. A method for monitoring vital signs of a human or animal subject, comprising;
   a) clothing the subject in a shirt or undershirt,
   b) removably attaching a carrier carrying a sensor to the shirt or undershirt adjacent the thoracic and abdominal regions of the subject;
   c) sensing elastic deformations of the shirt or undershirt corresponding to one or more of the group of vital signs comprising respiration, heart function, heart rhythm and associated sounds;
   d) generating electrical signals representative of the elastic deformations; and
   e) transmitting the signals from a transmitter to a receiver remote from the shirt or undershirt.

2. The method as claimed in claim 1, in which the shirt or undershirt is elastically deformable in a plurality of directions both longitudinally and laterally of the subject, and the sensor senses elastic deformations in the plurality of directions.

3. The method as claimed in claim 2, further comprising a step of storing the signals in a memory prior to transmission.

4. The method as claimed in claim 2, in which the transmitting of the signals occurs in periodic bursts, reducing average transmitter power consumption.

5. The method as claimed in claim 2, further comprising steps of;
   receiving the signals at the receiver;
   storing the signals in a memory; and
   processing the signals to extract data corresponding to the vital signs.

6. The method as claimed in claim 2, further comprising a step of displaying the data.

7. The method as claimed in claim 2, further comprising steps of:
   comparing the extracted data with predetermined criteria; and
   activating a signalling means if a difference is detected.

8. The method as claimed in claim 1, further comprising a step of storing the signals in a memory prior to transmission.

9. The method as claimed in claim 1, in which the transmitting of the signals occurs in periodic bursts, reducing average transmitter power consumption.

10. The method as claimed in claim 1, further comprising steps of:
    receiving the signals at the receiver;
    storing the signals in a memory; and
    processing the signals to extract data corresponding to the vital signals.

11. The method as claimed in claim 1, further comprising a step of displaying the data.

12. The method as claimed in claim 1, further comprising steps of:
    comparing the extracted data with predetermined criteria; and
    activating a signalling means if a difference is detected.

13. A system for monitoring vital signs from the thoracic and/or abdominal regions of a human or animal subject, comprising:
    a) a shirt or undershirt being elastically deformable for fitting the thoracic and abdominal regions of the subject closely;
    b) a carrier carrying a sensor, said carrier being removably attachable to said shirt or undershirt, the sensor being constructed to sense elastic deformations of the shirt or undershirt being caused by one or more of the group of vital signs of the subject comprising respiration, heart functions, heart rhythm and associated sounds, the sensor providing electrical signals in operation corresponding to the vital signs;
    c) a transmitter being carried by said carrier for transmitting the signals to a receiver remote from said shirt or undershirt by electromagnetic wave transmission; and
    d) a receiver for receiving the signals from said transmitter, said receiver being situated remote from said shirt or undershirt.

14. A system as claimed in claim 13, in which said shirt or undershirt is elastically deformable in a plurality of directions both longitudinally and laterally of the subject, the sensor sensing elastic deformations in the plurality of directions.

15. A system as claimed in claim 13, in which said carrier comprises a patch which is adapted to be placed on a specific region of the subject and which does not encircle the subject.

16. The system as claimed in claim 13, in which said carrier carries a plurality of sensors for sensing the vital signs of the subject in both the abdominal and thoracic regions.

17. The system as claimed in claim 13, in which said carrier is flexible.

18. The system as claimed in claim 13, in which said carrier comprises a piece of fabric.

19. The system as claimed in claim 13, in which said carrier is attached to the shirt or undershirt by a fabric fastening involving the inter-engagement of hook fibers and fibers of the shirt or undershirt.

20. The system as claimed in claim 13, in which said carrier is completely enclosable within a pocket of the shirt or undershirt.

21. The system as claimed in claim 13, in which said carrier is attached to the shirt or undershirt by an overlying fabric flap being secured to the shirt or undershirt.

22. A device for monitoring vital signs from a human or animal subject comprising an elastically deformable shirt or undershirt, comprising a carrier in the form of a patch which does not encircle the subject and which is removably attached to said shirt or undershirt, the carrier carrying a sensor and a transmitter means, the sensor being constructed to sense elastic deformations of the shirt or undershirt in a plurality of directions, corresponding to the vital signs of the given subject in operation and to generate corresponding signals for transmission by the transmitter means.

23. A device for monitoring vital signs from a human or animal subject wearing an elastically deformable shirt or undershirt as claimed in claim 22, in which the patch carries a source of electrical power.

24. The device as claimed in claim 23, further comprising memory means for storing the signals, characterized in that the signals are transmitted in periodic bursts thereby reducing average power consumption of the transmitter means.

25. The device as claimed in claim 22, further comprising memory means for storing the signals, characterized in that the signals are transmitted in periodic bursts thereby reducing average power consumption of the transmitter means.

* * * * *